United States Patent [19]

Green

[11] 4,229,369
[45] Oct. 21, 1980

[54] TRIS (HYDROXYMETHYL) AMINOMETHANE SALT OF 2-MERCAPTOSUCCINIC ACID

[75] Inventor: Stanley E. Green, Houston, Tex.

[73] Assignee: Hycel, Inc., Houston, Tex.

[21] Appl. No.: 33,105

[22] Filed: Apr. 25, 1979

Related U.S. Application Data

[62] Division of Ser. No. 849,790, Nov. 9, 1977, Pat. No. 4,189,536.

[51] Int. Cl.$^3$ .............................................. C07C 149/20
[52] U.S. Cl. .................................. 260/501.19; 435/14; 435/17; 435/188
[58] Field of Search ................................... 260/501.19

[56] References Cited

U.S. PATENT DOCUMENTS

| | | | |
|---|---|---|---|
| 3,271,248 | 9/1966 | Renault et al. | 260/501.19 |
| 3,540,984 | 11/1970 | Deutsch | 435/15 |
| 3,699,066 | 10/1972 | Hunsucker | 260/501.19 |

OTHER PUBLICATIONS

Oliver, J. Biochem., 61, pp. 116–122, (1955).
Rosalki, J. Clin. Lab. Med., 69, 696 (1967).
Talke et al., Klin Wochensche, 43, 174, (1965).
Barthelmai et al., Klin. Wschr., 40, 585, (1962).
Anido et al., Quality Control in Clinical Chem., pp. 180–183, (Walter de Gruyter, Berlin 1975).

*Primary Examiner*—G. T. Breitenstein
*Attorney, Agent, or Firm*—Robert P. Cogan; Tim L. Burgess

[57] ABSTRACT

An improved reagent system for chemical determinations and novel compositions therefor provide improved reagent stability, particularly in a dry, storage stable phase. For determinations in which hexokinase and glucose-6-phosphate dehydrogenase are indicator enzymes, glycine and taurine are combined with bovine serum albumin to provide a bulking agent for the indicator enzymes which also acts as a stabilizer. A novel salt, the tris (hydroxymethyl)aminomethane salt of 2 mercaptosuccinic acid, acts as an activator or stabilizer in chemistries utilizing the indicator enzymes, namely determinations of creatine phosphokinase or glucose. The novel salt also acts as a stabilizer in a urea nitrogen determination. Dry reagent components are bulked in triethanolammonium terepthalate. Novel CPK, glucose and serum urea nitogen determinations are also provided.

1 Claim, No Drawings

TRIS (HYDROXYMETHYL) AMINOMETHANE SALT OF 2-MERCAPTOSUCCINIC ACID

This is a division of application Serial No. 849,790 filed on Nov. 9, 1977, now U.S. Pat. No. 4,189,536.

BACKGROUND OF THE INVENTION

The present invention relates to improved compositions and methods for enzymatic determination of components in biological fluids.

The invention is initially discussed in the context of a creatine phosphokinase assay.

Creatine phosphokinase (CPK) is found primarily in muscle, brain, and heart tissue. Determination of CPK, particularly in blood serum, is one of the most sensitive enzyme assays available for the detection of skeletal muscle disease and is also useful in the diagnosis of myocardial infarction and cerebrovascular incidents.

A basic method for assaying for CPK is the method of C. Oliver, J. Biochem, Volume 61, page 116 (1955). The method has been modified by several workers for use as a diagnostic reagent, see for example, S. B. Rosalki, J. Clin. Lab. Med., Vol. 69, p. 696 (1967). The assay is based on the following principals:

CPK catalyzes the transfer of the phosphate group from creatine phosphate to adenosine diphosphate (ADP) in the presence of magnesium ions and preferably also sulfhydryl groups as activators:

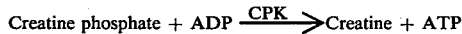

where ATP is adenosine phosphate. ATP is used to produce glucose-6-phosphate from glucose. This reaction is catalyzed by hexokinase (HK):

Glucose-6-phosphate is then oxidized by a nicotinamide adenine dinucleotide coenzyme, namely nicotinamide adenine dinucleotide phosphate (NADP) or nicotinamide adenine dinucleotide (NAD) in the presence of glucose-6-phosphate dehydroganase (G-6-PDH):

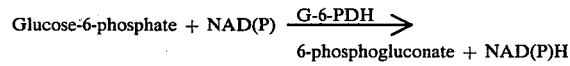

After an initial lag phase, the three reactions proceed stoichiometrically and quantitatively. The NAD(P)H, i.e. reduced NAD or reduced NADP, is determined spectrophotometrically at 340 nm. Alternatively, color coupling reagents may be added to enable spectrophotometric reading in the visible range, e.g. 500 nm.

In the above reaction, the enzymes HK and G-6-PDH may be referred to as indicator enzymes since they are used to convert reaction products into products which are spectrophotometrically measurable. The indicator enzymes in their purified form are used in a portion of about 30 micrograms per 40 milligrams of dry reagent, which is used to make one ml. of liquid reagent. Thus, two problems are presented. The first is that this extremely low percentage, i.e. 0.075% by weight of the dry mixture, is essentially difficult to mix. Therefore, a medium commonly referred to in the art as a bulking agent is needed in which the indicator enzymes may be mixed. Then the indicator enzymes may be uniformly dispersed within a dry mixture so that a conveniently measurable amount of the dry mixture may be used to provide a small amount of the indicator enzymes. This mixing in a medium of greater volume is commonly referred to as bulking. The second problem is that the bulking agent must be suitable for use in both a dry phase of the reagent for storage stability and in the aqueous reagent phase after it is mixed in an aqueous solution for use in assaying.

It is known in the art that it is desirable to provide a kit of several reagents to perform an assay and that providing reagents containing such components as enzymes, coenzymes and/or substrates a material in dry, solid form will be more stable and have a longer shelf-life than a liquid reagent. For example, such advantages are discussed in U.S. Pat. No. 3,540,984 to Alfred Deutsch, issued Nov. 17, 1970. A desired form of preparation of a dry powder enzyme reagent having a long shelf life comprises mixing reagent components in an aqueous solution and lyophilizing them to provide a stable, dry, enzyme-containing material. The enzyme-containing material is in turn mixed with other dry reagent components and with a further dry bulking agent in order to form an economical, conveniently manufactured form of a multicomponent reagent containing compounds which would not be stable over long periods of time in an aqueous phase.

A bulking agent must have the properties normally desirable, i.e. it must be millable, friable and mix well with reagent components. It is also highly desirable that the bulking agent have a salutory effect with respect to enzyme stability. Also, enzyme reactions are subject to interference from many different sources; enzyme activity may be inhibited by anyone of a number of substances. One material that has been used for bulking hexokinase and G-6-PDH is ammonium sulfate. In aqueous solution, this bulking agent ionizes into ammonium ions and sulfate ions. These ions have elevated ionic strength. It has been observed that the activity of CPK is inhibited by various ions such as ammonium and sulfate and by elevated ionic strength in solutions. The problem is therefore presented of stabilizing the CPK reagent in which indicator enzymes are stabilized in dry and in aqueous form without the use of bulking agents which form ions of elevated ionic strength, which may inhibit enzyme activity. In accordance with the present invention, improved bulking is provided for hexokinase and G-6-PDH as well as improved CPK and glucose determinations.

The determination of serum glucose is probably the most frequently performed test in the clinical laboratory, and often utilizes hexokinase and G-6-PDH. Many factors, both physiological and pathological, affect the circulating glucose level. Pathological states which tend to produce hyperglycemia include diabetes mellitus, uremia, hyperthyroidism, and hyperadrenalism. Hypoglycemia is found most commonly with excessive use of insulin and other antidiabetic drugs as well as in certain diseases of the pituitary and adrenals.

One significant commercial glucose determination is a modification of the method of Barthelmai and Czok, Klin. Wschr., Volume 40, page 585 (1962). Glucose is determined by the highly specific hexokinase and glucose-6-phosphate dehydrogenase enzyme system coupled in the final step to the reduction of nicotinamide adenine dinucleotide (NAD), the formation of reduced NAD (NADH) being monitored at 340 nm.

In this method, hexokinase (HK) with a magnesium activator catalyzes the phosphorylation of glucose in the sample by adenosine triphosphate (ATP):

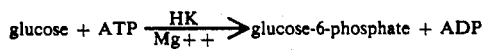

glucose + ATP $\xrightarrow[\text{Mg++}]{\text{HK}}$ glucose-6-phosphate + ADP where ADP is adenosine diphosphate.

Glucose-6-phosphate is then oxidized by a nicotinamide adenine dinucleotide coenzyme in the presence of glucose-6-phosphate dehydrogenase (G-6-PDH):

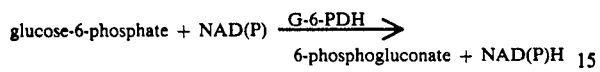

glucose-6-phosphate + NAD(P) $\xrightarrow{\text{G-6-PDH}}$ 6-phosphogluconate + NAD(P)H Both reactions proceed stoichiometrically and quantitatively. The NADH produced is determined spectrophotometrically at 340 nm.

Again, it is necessary to bulk and stabilize hexokinase and G-6-PDH. It is also desirable to provide a reagent system or kit in a dry, solid form.

In the quantities of reactive compounds for the above method for 1 ml. of reagent weigh about 15 mg. For example, the following components may be used:

0.03 mg. hexokinase
0.03 mg. glucose-6-PDH
0.4 mg. adenosine-triphosphate, sodium salt
0.6 mg. NAD
1.8 mg. magnesium maleate
12 mg. buffer material These weights of materials cannot be dispensed by commercial equipment with sufficient accuracy. A preferred weight of such a mixture should exceed 70 mg. or preferably 100 mg. Therefore, a dry powder bulking agent to bulk dry reagent components as well as enzyme-containing components is desirable. One such prior bulking agent is mannitol. It is also desirable to provide such a bulking agent which has further useful properties compared to mannitol, such as providing buffering and further contributing to stability. A new such bulking agent, triethanolammonium terephthatale (TEA-TPA), is provided in accordance with the invention.

Another important function in a reagent system is activation or stabilization of enzymes other than the above-defined indicator enzymes. In the present context, activation refers to reversing of oxidation or other adverse effect, while stabilization refers to the prevention thereof. It is important that the enzyme CPK maintain its enzyme activity since its action on the substrate creatine phosphate is necessary for the measurement of CPK in the biological fluid being tested. However, it is known that CPK loses some activity in some sera as a result of reversible inactivation due to the oxidation of essential sulfhydryl groups. This inactivation of CPK may be reversed in part or totally by adding to a reagent composition, and hence reacting with CPK, sulfhydryl-containing compounds such as glutathione, mercaptoacetic acid, or dithiothereitol (DTT). This may be accomplished by adding the compound to the serum or by incorporating it in the enzyme assay mixture. The most commonly used sulfhydryl compounds for this application are glutathione (GSH) and DTT.

However, it has been noticed that in the embodiment in which iodonitrotetrazolium violet (INT) coupling is provided for spectrophotometric measurement in the visible range, sulfhydryl compounds slowly reduce the INT to form its colored formazan. This increases the amount of background color, or may be said to increase the blank reaction. The range of the useful curve of optical absorbance versus concentration of CPK which is useful is thereby reduced. It should be noted that GSH and DTT in particular are quite expensive. GSH has also been criticized somewhat in the literature. For example, see G. Anido, S. B. Rosalki, E. J. van Kampen and M. Ruben, *Quality Control in Clinical Chemistry*, pp. 180–183, (Walter de Gruyter, Berlin, 1975). It is stated that definitive recommendations on the appropriate thiol cannot be made.

It is therefore desirable to find an activator for CPK which is also compatible with the other components in the reagent system. It is also preferable if that reagent is of lower cost. Another consideration is that the activator be useful in a dry, solid reagent system having a long shelf-life. The material selected must be useful in the initial reagent preparation, the dry phase, and again in the aqueous state when the reconstituted reagent is used in the laboratory. It is also desirable to provide an improved stabilizer for enzymes used for the determination of glucose and serum urea nitrogen. Such an activator stabilizer is provided in accordance with the present invention.

The determination of serum urea nitrogen, also often referred to as BUN, is widely used for evaluation of the kidney function. One standard method is that of H. Talke and G. E. Schubert, Klin.-Wschr. Vol. 43, p. 174 (1965). This enzymatic method does not require the use of corrosive reagents or high reaction temperatures.

This determination is based on the following principles:

Urea is hydrolyzed by urease:

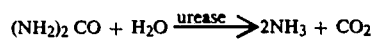

$(NH_2)_2 CO + H_2O \xrightarrow{\text{urease}} 2NH_3 + CO_2$

Ammonia is produced which aminates α-ketoglutarate in the presence of glutamate dehydrogenase (GLDH) with concurrent oxidation of NADH:

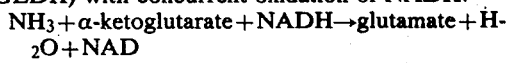

NH$_3$+α-ketoglutarate+NADH→glutamate+H$_2$O+NAD

Both reactions proceed stoichometrically and quantitatively. The disappearance of NADH is measured at 340 nm spectrophotometrically.

The novel activator and stabilizer of the present invention interacts in the CPK and glucose determinations described above and also interacts with the improved bulking agents referred to above to provide further improved CPK and glucose determinations. An improved serum urea nitrogen determination and improved stabilization of enzymes therein are also provided.

All of the elements described above cooperate to form an interactive reagent system. This concept is illustrated and defined by the example of the novel glucose reagent system. A novel bulking agent is provided for bulking indicator enzymes. This bulking agent improves stability in the dry phase. A further novel bulking agent is also provided for bulking other dry reagent components and also contributes to stability in the dry phase. The two bulking agents both contribute to stability while neither adversely affects the other. A novel enzyme stabilizer is also included in the dry reagent system. This stabilizer acts in the aqueous phase to improve reagent stability. The stabilizer does not adversely affect stability in the dry phase, and the bulking agents do not adversely affect stability in the aqueous phase. Also, the further bulking agent acts as a buffer in the aqueous phase. The bulking agents do not interfere with stability or with the chemical reactions in the aqueous phase. Compatability of reagent system components contributes to the desirable result of providing a reagent system which may be stored by a user on a shelf for prolonged periods of time before use and which is also stable for long periods of time in use. (The terms "prolonged" and "long" are used in their well-known sense in the context of clinical chemistry laboratory use.)

Stability is a significant aspect in the commercial use of reagents. A reagent with a long shelf life may remain in distribution channels such as in a manufacturer's and distributor's inventory before shipment to a laboratory, and the laboratory may order a sufficiently large inventory so that frequent reordering is not necessary. Increasingly critical cost factors are thus somewhat alleviated. In vitro diagnostic reagents must be discarded after expiration dates based on their stability, and it is important to provide a reagent which a laboratory will not need to return or discard before use.

SUMMARY OF THE INVENTION

It is therefor a general object of the present invention to provide improved reagent systems for CPK, glucose and urea nitrogen assays in which components thereof interact to improve reagent stability in the dry, storage stable phase and in the aqueous phase for performance of chemical determinations.

It is an object of the present invention to provide an improved bulking agent for the enzymes hexokinase or G-6-PDH.

It is a specific object of the present invention to provide a bulking agent for stabilizing hexokinase and G-6-PDH and which is of low ionic strength in aqueous solution.

It is a further object of the present invention to provide a bulking agent of the type described which also acts as a stabilizer.

It is another object of the present invention to provide a further bulking agent for bulking dry reagent system components, which components may include bulked enzymes.

It is a further object of the present invention to provide an improved CPK determination incorporating an improved bulking agent for indicator enzymes.

It is another object of the present invention to provide an improved glucose determination incorporating an improved bulking agent for indicator enzymes.

Additionally, it is another object of the present invention to provide a novel compositon useful as an enzyme activator or stabilizer.

It is a more specific object of the present invention to provide a compound useful as an activator in CPK and as a stabilizer in glucose or urea nitrogen determinations.

it is also an object of the present invention to provide a novel CPK reagent system and determination incorporating an improved activator.

It is another object of the present invention to provide a novel glucose reagent system and determination incorporating an improved stabilizer.

It is still another object of the present invention to provide a novel urea nitrogen determination incorporating an improved stabilizer.

It is a further object of the present invention to provide a novel CPK reagent system and determination incorporating a novel bulking agent and novel activator which cooperate to provide improved reagent stability in both the dry and aqueous phases.

It is also an additional object of the present invention to provide a novel glucose reagent system and determination incorporating improved bulking agents and a stabilizer which cooperate in the reagent system for improved stability of reagent in both the dry and aqueous phases.

It is another object of the present invention to provide a novel serum reagent system and determination incorporating a novel bulking agent and a stabilizer which cooperate in the reagent system for improved stability of reagent in both the dry and aqueous phases.

Briefly stated, in accordance with the present invention, a bulking agent for the indicator enzymes hexokinase and G-6-PDH is provided. The bulking agent comprises bovine serum albumin and glycine and taurine. A novel compound is prepared consisting of the tris (hydroxymethyl) aminomethane salt of 2-mercaptosuccinic acid which is useful as an activator in CPK determinations and as a stabilizer in glucose and serum urea nitrogen determinations. A further bulking agent for dry reagents is provided, comprising triethanolammonium terephthalate (TEA-TPA). Stable reagent systems for the respective determination of CPK and glucose of the type in which hexokinase and glucose-6-phosphate dehydrogenase are indicator enzymes are provided. Further, the novel bulking agents and activator-stabilizer cooperate in reagent systems to provide improved reagent stability in both the dry phase in storage and the aqueous phase in use. An improved stable reagent system is also provided for urea nitrogen determinations.

DESCRIPTION OF THE PREFERRED EMBODIMENTS

The invention is initially discussed in the context of a CPK assay. All temperatures recited below are centigrade.

Materials

A CPK reagent system requires creatine phosphate substrate, ADP, magnesium activator, NAD, glucose, sulfhydryl activator compound such as glutathione or a different composition such as that provided in the present invention, hexokinase such as from a yeast source, and G-6-PDH from a leuconostoc source. Alternatively, NADP may be used in place of NAD, and the G-6-PDH utilized may be from a leuconostoc or yeast source. Additionally, buffer materials, AMP, filler, binder and stabilizers, particularly for the hexokinase and G-6-PDH, are required. In the preferred form, the stabilizer is also the filler.

EXAMPLE I

In the preferred form, it is desired to provide a dry powder CPK reagent system which is reconstituted for laboratory assay use. The following materials are dried in vacuo to constant weight. Each dry material is milled or ground to fine powder. The resulting dry powders are mixed such as by agitation in a ball mill, V-blender, or other mixer until samples withdrawn from the mix are found to be homogeneous. Operations and handling of materials should be performed under conditions in which atmospheric moisture will not be absorbed in or adsorbed to the materials so as to make the resulting reagent have a shorter life. The following components are utilized to make sufficient reagent to be reconstituted with 100 liters of water.

For 100 liters of CPK Reagent:

| Preferred amount | |
|---|---|
| 300,000 IU | 100,000–600,000 IU at 37 degrees bulked, stabilized hexokinase |
| 300,000 IU | 100,000–600,000 IU at 37 degrees bulked, stabilized glucose-6-phosphate dehydrogenase |
| 76g | 38–152 g. d-Glucose |
| 200g | 67–400 g nicotinamide-adenine dinucleotide free acid |
| 280g | 100–350 g magnesium maleate |
| 125g | 90–300 g adenosine diphosphate, trilithium salt |
| 1060g | 875–2430g Disodium creatine phosphate dried to 1 mole or less of water of crystallization |
| 285g | 150–275g adenosine monophosphoric desodium salt |
| 158g | 100–200g tris (hydroxymethyl)aminomethane salt of 2-mercaptosuccinic acid (TMS) |
| | ** tris (hydroxymethyl)aminomethane free base |
| | ** N-tris-(hydroxymethyl) methyl-2 amino - ethanesulfonic acid |
| | ** These are the buffering components added to produce the desired final pH 6.9 (6.7–7.2) |
| | * The 100 liters refers to the volume of water to be added to the dry reagent form to make the liquid form used for performing the test. |

The components above are homogeneously mixed. The total weight is observed or calculated from the sum of the component weights. The total weight in grams divided by 100,000 grams of dry reagent to be dissolved in 1 ml of water to form the aqueous reagent for laboratory use. In the preferred form, the powder mixture is packaged in butyl rubber stopper serum vials with powder sufficient for addition of 25 ml of water. The powder may be dispensed by utilizing known equipment, an example of which is the powder dispenser known by the trademark ACCO-FIL manufactured by Perry Industries.

It is noted that this reagent composition does not comprise a sulfhydryl compound such as glutathione (GSH) for activation of CPK. The reagent includes the tris (hydroxymethyl) aminomethane salt of 2-mercaptosuccinic acid. This salt is abbreviated herein as TMS.

TMS is a new substance prepared as described below in Example III. It has been discovered that TMS prevents or reverses the oxidation of CPK. Further, it aids in stabilizing the hexokinase and G-6-PDH components of the reagent system. TMS is also useful in an assay system because it is not a substrate for GSH dehydrogenase. GSH dehydrogenase is present in human cells and may be present in serum samples being assayed. The use of TMS in an activator system prevents the possibility of the activator reacting with the serum as may occur when GSH is used as the activator. Additionally, applicant has obtained glutathione at a cost of $353 per mole and DTT at $942 per mole (one mole of DTT being equivalent to two moles of GSH), while obtaining mercaptosuccinic acid at $21 per mole. There is approximately 0.01 mole of either substance used for 1 liter of reconstituted reagent.

CPK Determination

In the preferred utilization of the above reagent system, dry reagent powder is dissolved in deionized water.

The components above are homogeneously mixed. The total weight is observed or calculated from the sum of the component weights. The total weight in grams divided by 100,000 is grams of dry reagent to be dissolved in 1 ml of water to form the aqueous reagent for laboratory use. In the preferred form, the powder mixture is packaged in butyl rubber stopper serum vials with powder sufficient for addition of 25 ml of water. The powder may be dispensed by utilizing known equipment, an example of which is the powder dispenser known by the trademark ACCO-FIL manufactured by Perry Industries.

It is noted that this reagent composition does not comprise a sulfhydryl compound such as glutathione (GSH) for activation of CPK. The reagent includes the tris (hydroxymethyl) aminomethane salt of 2-mercaptosuccinic acid. This salt is abbreviated herein as TMS.

TMS is a new substance prepared as described below in Example III. It has been discovered that TMS prevents or reverses the oxidation of CPK. Further, it aids in stabilizing the hexokinase and G-6-PDH components of the reagent system. TMS is also useful in an assay system because it is not a substrate for GSH dehydrogenase. GSH dehydrogenase is present in human cells and may be present in serum samples being assayed. The use of TMS in an activator system prevents the possibility of the activator reacting with the serum as may occur when GSH is used as the activator. Additionally, applicant has obtained glutathione at a cost of $353 per mole and DTT at $942 per mole (one mole of DTT being equivalent to two moles of GSH), while obtaining mercaptosuccinic acid at $21 per mole. There is approximately 0.01 mole of either substance used for 1 liter of reconstituted reagent.

CPK Determination

In the preferred utilization of the above reagent system, dry reagent powder is dissolved in deionized water. The powder should not be exposed to air for prolonged periods of time before dissolution. A spectrophotometer is provided, set to 340 nm and allowed to stabilize. The spectrophotometer is "zeroed", i.e. set against an appropriate blank such as air or water.

The reagent is incubated in a cuvette at 37° C. for 10 minutes. A sample is added thereto, and mixed thoroughly with the reagent. The cuvette is incubated, preferably in a thermostated spectrophotometer compartment. Two minutes after addition of the sample, a first optical absorbance reading A1 of the reaction mixture is read. Five minutes thereafter, a second absorbance reading A2 is taken.

To calculate CPK activity in units per liter, U/L, $\Delta A$ is calculated.

$$\Delta A = A1 - A2$$

$$U/L = \Delta A \times F$$

When a 1 cm lightpath through the cuvette is provided:

$$F = \frac{1}{t} \times \frac{TV}{SV} \times \frac{1000}{10^{-6}} \times e$$

where t is the time interval between the taking of readings A1 and A2,

TV is the total reaction volume in ml,

SV is the sample volume in ml, and e is the molar extinction coefficient of NADH at 340 nm ($6.22 \times 10^6$)

where t=5 min, TV=2.15 ml, and SV=0.05 ml, then F=1382.

EXAMPLE II

A reagent system was prepared in accordance with Example I, but included further components for color coupling. A preferred color coupling component is iodonitrotetrazolium violet (INT), which is reduced by NAD to form its colored formazan whose optical absorbance is measured in the range of 505 nm. It is well known to perform this reaction in the presence of an electron asceptor such as diaphorase or phenazine methyl sulfate (PMS). Diaphorase may be stabilized in accordance with Example VI. From 50,000 to 300,000 international units, preferably 100,000 IU, may be added to the formulation of Example I.

Assays were performed utilizing the mixture. It is found that TMS provides the antioxidant properties, as does GSH or other sulfhydryl compounds. However, it is also noted that TMS does not react significantly with INT, while reaction of GSH with INT reduces INT to form a colored product. This reaction of GSH increases the blank reaction and thereby reduces the useful range of the CPK assay. The use of TMS thus permits for maintaining a full useful range of optical absorbance of reaction products versus concentration units of CPK therein.

In use of the reagent, the well-known factor accounting for the reduction of INT is utilized rather than the molar extinction coefficient of NADH at 340 nm.

EXAMPLE III

It has been found that the presence of TMS in a reagent prepared in accordance with Example I is at least as effective in activating CPK as GSH is in a similar reagent. In the absence of TMS, CPK activity was lost upon a sample's standing and was not initially recovered from the sample. TMS also prevents oxidation of enzymes in the above-described glucose and urea nitrogen determinations. It is for this reason TMS is referred to herein as an activator and stabilizer.

The preparation of TMS may be accomplished by the following method. To ten liters of water, 1.5 kg of mercaptosuccinic acid is added. Solid tris (hydroxymethyl)aminomethane (TRIS) is added with stirring until the resulting solution is at a pH of 6.8–7. This solution is frozen in a dry ice bath and lyophilized. The lyophilization results in a glassy material. This material is washed with acetone. The resulting mass is placed in ten liters of methanol, warmed and agitated. A white solid forms. When the white solid forms, ten liters of acetone are added. The product is collected by filtration, washed and dried to provide TMS. Alternatively for producing a CPK reagent in accordance with Example I, to the solution to be lyophilized may be added the requisite amount of AMP disodium salt. The lyophilization is carried out. In this case, the lyophilizate does not require the acetone treatment.

EXAMPLE IV

TMS is also useful in a glucose reagent. For 100 liters of reagent, the following components may be used.

| Preferred Amount | |
|---|---|
| 60g | 40–240g NAD |
| 180g | 100–350g Magnesium maleate |
| 40g | 20–120g adenosine triphosphate disodium salt, preferably |
| 250g | 100–400g TMS |
| 200,000 IU | 100,000–600,000 IU at 37 degrees bulked stabilized hexokinase |
| 250,000 IU | 100,000–600,000 IU at 37 degrees bulked stabilized G-6-PDH |
| 1000g | 500–2000g Triethanol amine salt of terepthalic acid (TEA-TPA) (prepared in accordance with Example V) tris (hydroxymethyl)aminomethane sufficient to create a pH of 7.2–7.8 in reagent when dissolved in water. |

It is useful to provide a magnesium salt as a source of magnesium ions. However, many magnesium salts are quite hygroscopic. Absorbance of water may adversely affect stability. Magnesium maleate is selected above since it is not hygroscopic. Other non-hygroscopic salts to provide activator ions may be used.

Glucose Determination

In the preferred utilization of the above reagent system, dry reagent powder is dissolved in deionized water. The powder should not be exposed to air for prolonged periods of time before dissolution. A spectrophotometer is provided, set to 340 nm, and allowed to stabilize. The spectrophotometer is "zeroed", i.e. set against an appropriate blank such as air or water.

The reagent is placed in a cuvette and a first absorbance reading A0 is taken. Sample is mixed in each cuvette and the resulting reaction mixture is incubated at room temperature for between 5 and 30 minutes. A second absorbance reading A is taken. A0 is subtracted from A to yield ΔA sample. A standard is similarly tested to obtain a value of ΔA standard.

$$\text{glucose concentration} = \frac{\Delta A \text{ sample} \times C}{\Delta A \text{ standard}}$$

Where C is the glucose concentration in the standard. It should be noted that grossly icteric, hemolyzed or lipemic specimens may require a blank correction so that a term is provided for subtraction from A sample to compensate for optical absorbance not due to the presence of glucose.

EXAMPLE V

TEA-TPA is a novel bulking agent preferably used for bulking dry reagents, particularly for glucose and urea nitrogen reagents.

To prepare TEA-TPA, for example, 20 liters of water may be used to which are added 9.25 kg triethenolamine and 4.5 kg terephthalic acid. The solution is heated to 60 degrees centigrade and then allowed to cool to less than 40 degrees centigrade. Thereafter, 80 liters of acetone are added slowly. The solution is cooled. A fine white precipitate which forms is collected by filtration and washed and dried to provide TEA-TPA.

EXAMPLE VI

A similar preparation was also prepared to measure urea nitrogen in a determination in which urea is hydrolyzed by urease, ammonia is produced to aminate α-ketoglutarate in the presence of glutamate dehydrogenase with the concurrent oxidation of NADH which may be monitored spectrophotometrically. Again, the TMS was found to stabilize indicator enzymes.

A dry urea nitrogen reagent system which may be reconstituted to 100 liters of reagent is prepared from:

| Preferred Amount | |
|---|---|
| 128g | 60-360g α-ketoglutarate (alpha) |
| 27.5g | 20-55g NADH (yeast source) |
| 200g | 0-400g ADP, trilithium salt |
| 800,000 IU | 400,000-1,200,000 IU urease |
| 1,200,000 IU | 600,000-2,400,000 IU glutamate dehydrogenase (beef liver source) |
| 1000g | 200-12,000g TEA-TPA |
| 200g | 100-400g TMS |
| | tris (hydroxymethyl)aminomethane sufficient to produce a pH of 7.6±0.3 |

Urea Nitrogen Determination

In the preferred utilization of the above reagent system, dry reagent powder is dissolved in deionized water. The powder should not be exposed to air for prolonged periods of time before dissolution. A spectrophotometer is provided, set to 340 nm, and allowed to stabilize. The spectrophotometer is "zeroed", i.e. set against an appropriate blank such as air or water.

The reagent is placed in a cuvette and a first absorbance reading A0 is taken. Sample is mixed in each cuvette and the resulting reaction mixture is incubated at room temperature for 15 minutes. A second absorbance reading A is taken. A is subtracted from A0 to yield ΔA sample. A standard is similarly tested to obtain a value of ΔA standard.

$$\text{urea nitrogen concentration} = \frac{\Delta A \text{ sample} \times C}{\Delta A \text{ standard}}$$

Where C is the urea nitrogen concentration in the standard. It should be noted that grossly icteric, hemolyzed or lipemic specimens may require a blank correction so that a term is provided for addition to ΔA sample to compensate for the change in absorbance, or optical density, not due to the presence of urea nitrogen.

EXAMPLE VII

Preparation of bulked, stabilized hexokinase, glucose-6-phosphate dehydrogenase and/or diaphorase.

Each enzyme, HK, G-6-PDH or diaphorase, may be bulked together or separately, depending on the convenience of the manufacturing procedure. A stabilized solution is prepared and lyophilized to provide an enzyme-containing material. The material may be ground to provide a powder for combination with other reagent materials. To this solution is added 750,000 IU hexokinase, such as from a yeast source, and 750,000 IU G-6-PDH (leuconostoc).

Preparation of Stabilizer Solution for HK and G-6-PDH.

2-3L 30% bovine serum albumin solution
60-120 g glycine 24-96 g taurine

Sufficient water to produce 12 liters of solution to which either dilute hydrochloric acid or tris (hydroxymethyl)aminomethane is added to give a pH of 6.8±0.1.

A preferred set of actual values is 2.4 liters bovine albumin solution, 96 grams glycine, 48 grams taurine and 9.6 liters of water.

EXAMPLE VIII

A reagent may be prepared in accordance with Example I utilizing bulked stabilized hexokinase and G-6-PDH in accordance with Example VII and including a sulfhydryl compound other than TMS. For example, GSH or DTT may be utilized.

EXAMPLE IX

A reagent is prepared in accordance with Examples II or VIII and a tetrazolium salt such as INT is used in the reagent for color coupling. The INT is reduced by the NADPH or NADH to form its colored formazan for spectrophotometric reading at 505 nm. For INT color coupling, it is necessary to use an electron acceptor such as phenazine methylsulfate, PMS, or preferably diaphorase in a strength of 50,000 to 300,000 IU in the bulk stabilized form. A strength of 100,000 IU is preferred in the above mixture. To prepare bulked, stabilized diaphorase, 50,000 to 300,000 units of diaphorase are added to the previously described stabilizer solution of Example VII. The diaphorase may be prepared together with the other two enzymes or separately.

EXAMPLE X

The stabilized indicator enzymes of Example VII are utilized in the reagent of Example I.

EXAMPLE XI

The stabilized indicator enzymes of Example VII are utilized in the reagent of Example II.

EXAMPLE XII

A glucose reagent is produced according to Example IV utilizing an activator other than TMS, e.g. GSH, and bulked stabilized indicator enzymes in accordance with Example VII.

EXAMPLE XIII

A glucose reagent is produced in accordance with Example IV utilizing bulked, stabilized indicator enzymes in accordance with Example VII.

EXAMPLE XIV

A glucose reagent is produced in accordance with Examples IV or XII utilizing mannitol as a bulking agent for dry reagent components in place of TEA-TPA.

EXAMPLE XV

A urea nitrogen reagent is produced in accordance with Example VI utilizing mannitol as a bulking agent for dry reagent components in place of TEA-TPA.

EXAMPLE XVI

A urea nitrogen reagent is produced in accordance with Example VI utilizing a sulfhydryl compound other than TMS, such as GSH or DTT.

It is seen that in the reagent systems and determinations above, stability in both the dry, storage stable state and in the aqueous state for use is provided. In addition, individual components of those which cooperate are unique. The specification will enable those skilled in the art to practice many specific forms of the invention in accordance with the above teachings.

What is claimed as new and desired to be secured by Letters Patent of the United States is:

1. The tris(hydroxymethyl)aminomethane salt of 2-mercaptosuccinic acid.

* * * * *